United States Patent

Ourada

[11] Patent Number: 6,027,521
[45] Date of Patent: Feb. 22, 2000

[54] BEHAVIOR MODIFICATION REINFORCEMENT BRACELET

[76] Inventor: Rosemarie A. Ourada, 4416 Prospect Ave., Downers Grove, Ill. 60515-2911

[21] Appl. No.: 09/247,991

[22] Filed: Feb. 11, 1999

[51] Int. Cl.[7] .................................................. A61B 17/00
[52] U.S. Cl. ............................................................ 606/204
[58] Field of Search ...................................... 606/201–204

[56] References Cited

U.S. PATENT DOCUMENTS

| | | | |
|---|---|---|---|
| 5,234,459 | 8/1993 | Lee | 606/203 |
| 5,312,350 | 5/1994 | Jacobs | 606/201 |
| 5,601,598 | 2/1997 | Fisher | 606/204 |
| 5,848,981 | 12/1998 | Herbranson | 606/204 |

*Primary Examiner*—Michael Buiz
*Assistant Examiner*—Vikki Trinh

[57] ABSTRACT

A behavior modification reinforcement bracelet for providing mildly painful stimuli to a user when the user thinks about or performs a behavior that the user wishes to change. The behavior modification reinforcement bracelet includes an elastic annular band with opposite inwards and outwards faces, and a pair of side edges. A plurality of stimuli regions are provided on the band. Each of the stimuli regions has a plurality of nubs extending in a radially inwards direction from the inwards face of the band.

8 Claims, 2 Drawing Sheets

BEHAVIOR MODIFICATION REINFORCEMENT BRACELET

BACKGROUND OF THE INVENTION

1. Field of the Invention

The present invention relates to behavior modification reinforcement devices and more particularly pertains to a new behavior modification reinforcement bracelet for providing mildly painful stimuli to a user when the user thinks about or performs a behavior that the user wishes to change.

2. Description of the Prior Art

The use of behavior modification reinforcement devices is known in the prior art. More specifically, behavior modification reinforcement devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,501,697 by Fisher; U.S. Pat. No. 3,889,163 by Symmes; U.S. Pat. No. 5,468,220 by Sucher; U.S. Pat. No. 5,078,728 by Giarratano; U.S. Pat. No. 2,068,173 by Galves; and U.S. Pat. No. Des. 344,177 by Mennie et al.

While these devices fulfill their respective, particular objectives and requirements, the aforementioned patents do not disclose a new behavior modification reinforcement bracelet. The inventive device includes an elastic annular band with opposite inwards and outwards faces, and a pair of side edges. A plurality of stimuli regions are provided on the band. Each of the stimuli regions has a plurality of nubs extending in a radially inwards direction from the inwards face of the band.

In these respects, the behavior modification reinforcement bracelet according to the present invention substantially departs from the conventional concepts and designs of the prior art, and in so doing provides an apparatus primarily developed for the purpose of providing mildly painful stimuli to a user when the user thinks about or performs a behavior that the user wishes to change.

SUMMARY OF THE INVENTION

In view of the foregoing disadvantages inherent in the known types of behavior modification reinforcement devices now present in the prior art, the present invention provides a new behavior modification reinforcement bracelet construction wherein the same can be utilized for providing mildly painful stimuli to a user when the user thinks about or performs a behavior that the user wishes to change.

The general purpose of the present invention, which will be described subsequently in greater detail, is to provide a new behavior modification reinforcement bracelet apparatus and method which has many of the advantages of the behavior modification reinforcement devices mentioned heretofore and many novel features that result in a new behavior modification reinforcement bracelet which is not anticipated, rendered obvious, suggested, or even implied by any of the prior art behavior modification reinforcement devices, either alone or in any combination thereof.

To attain this, the present invention generally comprises an elastic annular band with opposite inwards and outwards faces, and a pair of side edges. A plurality of stimuli regions are provided on the band. Each of the stimuli regions has a plurality of nubs extending in a radially inwards direction from the inwards face of the band.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new behavior modification reinforcement bracelet apparatus and method which has many of the advantages of the behavior modification reinforcement devices mentioned heretofore and many novel features that result in a new behavior modification reinforcement bracelet which is not anticipated, rendered obvious, suggested, or even implied by any of the prior art behavior modification reinforcement devices, either alone or in any combination thereof.

It is another object of the present invention to provide a new behavior modification reinforcement bracelet which may be easily and efficiently manufactured and marketed.

It is a further object of the present invention to provide a new behavior modification reinforcement bracelet which is of a durable and reliable construction.

An even further object of the present invention is to provide a new behavior modification reinforcement bracelet which is susceptible of a low cost of manufacture with regard to both materials and labor, and which accordingly is then susceptible of low prices of sale to the consuming public, thereby making such behavior modification reinforcement bracelet economically available to the buying public.

Still yet another object of the present invention is to provide a new behavior modification reinforcement bracelet which provides in the apparatuses and methods of the prior art some of the advantages thereof, while simultaneously overcoming some of the disadvantages normally associated therewith.

Still another object of the present invention is to provide a new behavior modification reinforcement bracelet for providing mildly painful stimuli to a user when the user thinks about or performs a behavior that the user wishes to change.

Yet another object of the present invention is to provide a new behavior modification reinforcement bracelet which includes an elastic annular band with opposite inwards and outwards faces, and a pair of side edges. A plurality of stimuli regions are provided on the band. Each of the stimuli regions has a plurality of nubs extending in a radially inwards direction from the inwards face of the band.

Still yet another object of the present invention is to provide a new behavior modification reinforcement bracelet that helps a user stop doing bad habits and behaviors such as smoking and swearing. For example, when the use has the desire to smoke or actually does smoke, the user would then use the bracelet to provide mildly painful stimuli to reinforce quitting smoking.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
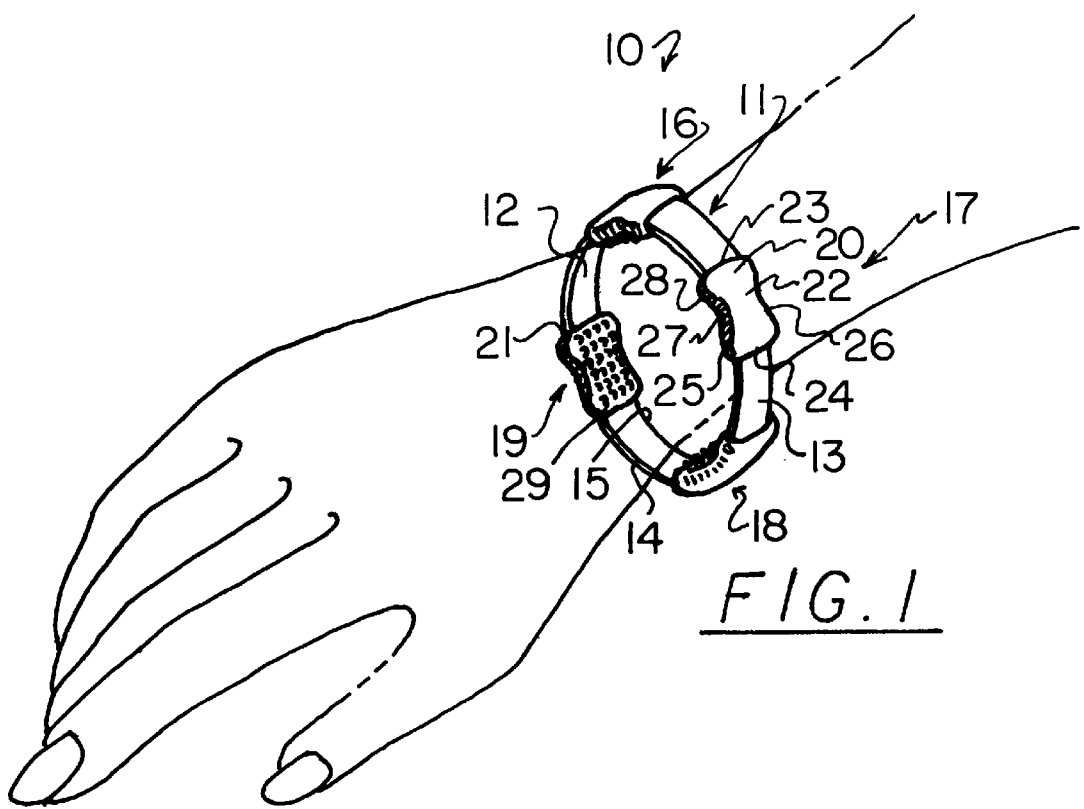
FIG. 1 is a schematic perspective view of a new behavior modification reinforcement bracelet according to the present invention.
Figure 2:
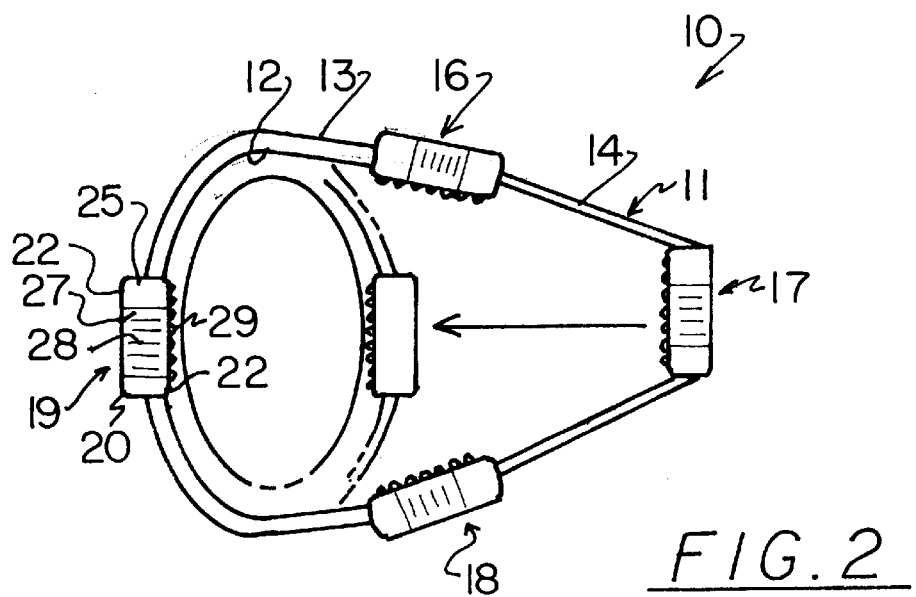
FIG. 2 is a schematic side view of the present invention illustrating the use of the present invention on the wrist of a user. This figure illustrates the stretched position from which the band is released to snap against the wrist of the user to inflict mildly painful stimuli with the nubs of the stimuli regions.
Figure 3:
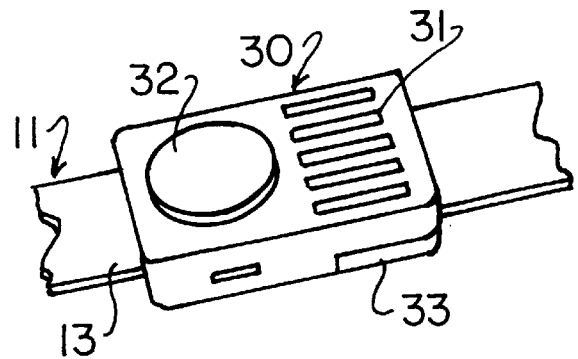
FIG. 3 is a schematic perspective view of the sound generating device on the band.

With reference now to the drawings, and in particular to FIGS. 1 through 6 thereof, a new behavior modification reinforcement bracelet embodying the principles and concepts of the present invention and generally designated by the reference numeral 10 will be described.

As best illustrated in FIGS. 1 through 6, the behavior modification reinforcement bracelet 10 generally comprises an elastic annular band with opposite inwards and outwards faces, and a pair of side edges. A plurality of stimuli regions are provided on the band. Each of the stimuli regions has a plurality of nubs extending in a radially inwards direction from the inwards face of the band.

In use, the bracelet is designed for providing a mildly painful stimuli for reinforcing behavior modification of a user. When a user thinks about or performs a behavior that the user is trying to change, the user snaps the bracelet for providing mildly painful stimuli to discourage the behavior or the thought of the behavior. For example, for a user attempting to quit smoking, every time the user thinks about smoking or does smoke, the user would then snap the bracelet to inflict pain which in turn will discourage the user from smoking.

In closer detail, the bracelet 10 comprises an elastic annular band 11 for wear on a user's wrist. The band has opposite inwards and outwards faces 12,13, and a pair of generally circular side edges 14,15. The band comprises an elastically stretchable material to permit resilient stretching of the band. Ideally, the band comprises an elastic woven or braided (such as macramé) material. In an ideal illustrative embodiment, the band has a width defined between the side edges of the band of about ⅝ inch, and a thickness defined between the inwards and outwards faces of the band of about ⅛ inch. Optionally, the bracelet may take the form of a strap having a pair of free ends that are detachably attached together by a fastener such as a buckle or a hook and loop fastener.

A plurality of stimuli regions 16,17,18,19 are provided on the band. Preferably, the stimuli regions are spaced apart at generally equal intervals along the band. Each of the stimuli regions comprises a resiliently deformable rectangular block 20 having inner and outer faces 21,22, a pair of opposite ends 23,24, and a pair of sides 25,26 extending between the ends of the respective block. The blocks each have a slot extending therethrough between the ends of the respective block through which the band is extended such that the blocks are attached to the band.

Preferably, as illustrated in FIG. 1, each side of each block has a generally concave portion 27 designed for receiving the fingers of a user pinching the sides of the respective block to permit pulling of the respective block away from the wrist of the user. The concave portions of the sides of the blocks ideally each have a plurality of ridges 28 for frictionally enhancing contact between the user's finger and the sides of the respective block.

Figure 4:
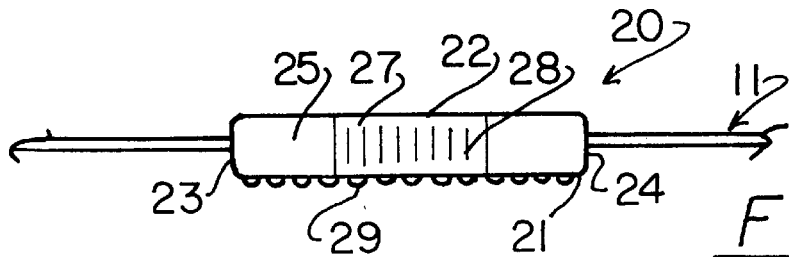
FIG. 4 is a schematic side view of hemispherical nubs of the present invention.
Figure 5:
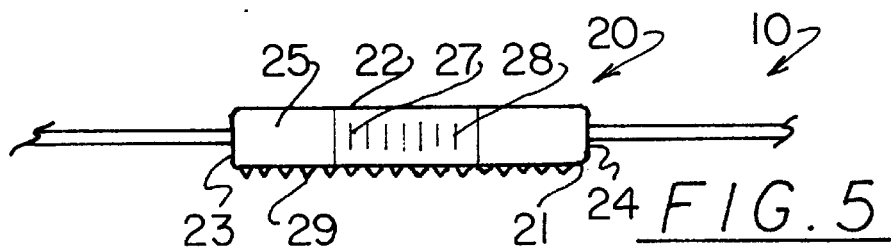
FIG. 5 is a schematic side view of triangular nubs of the present invention.

Each of the stimuli regions also has a plurality of nubs 29 extending in a radially inwards direction from the inwards face of the band. The nubs of each stimuli region are outwardly extended from the inner face of the associated block of the respective stimuli region. In use, the nubs are designed for poking the skin of a user to provide mildly painful stimuli to the user when the band is snapped against the skin of the user. In one preferred embodiment, as shown in FIG. 4, the nubs are each generally hemispherical in shape. In another preferred embodiment, as shown in FIG. 5, the nubs are each generally triangular or pyramidal in shape. Ideally, the nubs comprise a material more rigid than the block to ensure that they provide pain to the user's wrist. Ideally, each of the stimuli regions has twelve nubs arranged in four substantially parallel rods of five nubs each on the inner face of the associated block.

Figure 6:
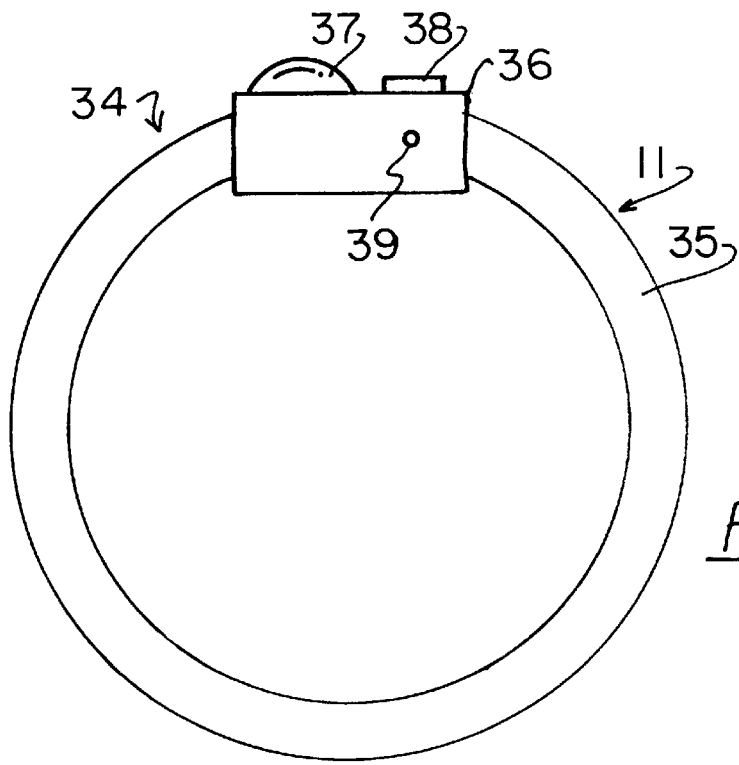
FIG. 6 is a schematic side view of the inflatable bladder embodiment of the present invention.

Optionally, a sound generating device 30 may be coupled to the band for generating an audible verbal message, such as, for example, the message "Stop that!" in a maternal authoritarian voice for reinforcing the behavior modification of the user. The sound generating device has a speaker 31 for projecting the audible verbal, message and an actuator 32 for activating generation of the audible verbal message. The sound generating device also preferably has a battery power source therein for providing energy to the sound generating device. The battery power source is preferably removable from the sound generating device via an access panel 33 in the sound generating device FIG. 6 illustrates another embodiment of the present invention 34. In this embodiment, the annular band comprises an annular inflatable bladder 35 with a pump 36 coupled to the inflatable bladder for pumping air into the inflatable bladder to inflate the inflatable bladder. The more the inflatable bladder is inflated, the more the inflatable bladder constricts around the wrist of the user to provide a constricting pain to the wrist of the user. The pump has a push actuator 37 for designed for depression with the finger or thumb of a user to pump air into the inflatable bladder with the pump. The pump has a depressible release valve 38 providing a closeable opening into the inflatable bladder to permit deflation of the inflatable bladder through an air hole 39 in the pump.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bracelet for permitting a user to provide stimuli to the user subsequent to a pre-determined event for providing negative reinforcement, said bracelet comprising:

an elastic annular band, said band having opposite inwards and outwards faces, and a pair of generally circular side edges;

a plurality of stimuli regions being provided on said band; and each of said stimuli regions having a plurality of nubs extending in a radially inwards direction from said inwards face of said band; and wherein each of said stimuli regions further comprises a resiliently deformable rectangular block having inner and outer faces, a pair of opposite ends, and a pair of sides extending between said ends of the respective block, said blocks each having a slot extending therethrough between said ends of the respective block, said band being extended through said slots of said block.

2. The bracelet of claim 1, wherein said band comprises an elastically stretchable material to permit resilient stretching of said band.

3. The bracelet of claim 1, wherein said stimuli regions are space apart at generally equal intervals along said band.

4. The bracelet of claim 3, wherein said nubs of each stimuli region are outwardly extended from said inner face of the associated block of the respective stimuli region.

5. The bracelet of claim 1, wherein said nubs are each generally hemispherical in shape.

6. The bracelet of claim 1, wherein said nubs are each generally triangular in shape.

7. A bracelet for providing stimuli for reinforcing behavior modification of a user, said bracelet comprising:

an elastic annular band, said band having opposite inwards and outwards faces, and a pair of generally circular side edges;

a plurality of stimuli regions being provided on said band; and each of said stimuli regions having a plurality of nubs extending in a radially inwards direction from said inwards face of said band; and a sound generating device being coupled to said band for generating an audible verbal message, said sound generating device having a speaker for projecting said audible verbal message, and wherein said sound generating device has an actuator for activating generation of said audible verbal message.

8. A bracelet for providing stimuli for reinforcing behavior modification of a user, said bracelet comprising:

an elastic annular band for wear on a user's wrist, said band having opposite inwards and outwards faces, and a pair of generally circular side edges, said band comprising an elastically stretchable material to permit resilient stretching of said band;

a plurality of stimuli regions being provided on said band, wherein said stimuli regions are space apart at generally equal intervals along said band;

each of said stimuli regions comprising a resiliently deformable rectangular block having inner and outer faces, a pair of opposite ends, and a pair of sides extending between said ends of the respective block;

said blocks each having a slot extending therethrough between said ends of the respective block, said band being extended through said slots of said block;

each of said stimuli regions having a plurality of nubs extending in a radially inwards direction from said inwards face of said band;

said nubs of each stimuli region being outwardly extended from said inner face of the associated block of the respective stimuli region; and a sound generating device being coupled to said band for generating an audible verbal message, said sound generating device having a speaker for projecting said audible verbal message said sound generating device having an actuator for activating generation of said audible verbal message, said sound generating device having a battery power source therein for providing energy to said sound generating device.

* * * * *